US009410922B2

(12) United States Patent
Lehle et al.

(10) Patent No.: US 9,410,922 B2
(45) Date of Patent: Aug. 9, 2016

(54) METHOD FOR ADJUSTING A GAS SENSOR
(71) Applicant: ROBERT BOSCH GMBH, Stuttgart (DE)
(72) Inventors: Hartwig Lehle, Stuttgart (DE); Lothar Diehl, Gemmrigheim (DE); Jochen Betten, Stuttgart (DE); Moritz Waldorf, Stuttgart (DE); Thomas Seiler, Stuttgart (DE)
(73) Assignee: ROBERT BOSCH GMBH, Stuttgart (DE)
( * ) Notice: Subject to any disclaimer, the term of this patent is extended or adjusted under 35 U.S.C. 154(b) by 302 days.
(21) Appl. No.: 14/351,867
(22) PCT Filed: Sep. 25, 2012
(86) PCT No.: PCT/EP2012/068829
§ 371 (c)(1),
(2) Date: Apr. 14, 2014
(87) PCT Pub. No.: WO2013/056943
PCT Pub. Date: Apr. 25, 2013
(65) Prior Publication Data
US 2014/0238102 A1  Aug. 28, 2014
(30) Foreign Application Priority Data
Oct. 18, 2011 (DE) .......................... 10 2011 084 734
(51) Int. Cl.
*G01N 27/417* (2006.01)
*G01N 27/406* (2006.01)
(Continued)
(52) U.S. Cl.
CPC ........ *G01N 27/4175* (2013.01); *G01N 27/4065* (2013.01); *G01N 27/407* (2013.01); *G01N 27/419* (2013.01); *G01N 33/0006* (2013.01); *G01N 33/007* (2013.01)
(58) Field of Classification Search
CPC ............ G01N 27/419; G01N 27/4065; G01N 27/4175
See application file for complete search history.

(56) References Cited

U.S. PATENT DOCUMENTS 4,384,935 A   5/1983  De Jong
6,551,499 B1 * 4/2003  Springhorn .......... G01N 27/419
                                                  204/401
(Continued)

FOREIGN PATENT DOCUMENTS

DE   10 2008 007 238    8/2009
DE      102008007238    8/2009
(Continued)

OTHER PUBLICATIONS

International Search Report for PCT/EP2012/068829, dated Jan. 16, 2013.

*Primary Examiner* — Peter Macchiarolo
*Assistant Examiner* — Nathaniel Kolb
(74) *Attorney, Agent, or Firm* — Norton Rose Fulbright US LLP

(57) ABSTRACT

In a method for adjusting a gas sensor having a hollow chamber connected to a measuring gas chamber and having an electrochemical pump cell electrochemically pumping the gas component into or out of the hollow chamber, at least two pumping-in phases are provided in which the gas component is pumped into the hollow chamber by the electrochemical pump cell, and at least two pumping-out phases are provided in which the gas component is pumped out of the hollow chamber by the electrochemical pump cell. On the basis of at least one feature of the pump current during the pumping-out phases ($M_{out}$), at least one piece of information for adjusting the gas sensor is generated. A parameter regarding the pumping-in is predefined differently in the at least two pumping-in phases.

15 Claims, 3 Drawing Sheets

(51) Int. Cl.
*G01N 27/407* (2006.01)
*G01N 27/419* (2006.01)
*G01N 33/00* (2006.01)

(56) References Cited

U.S. PATENT DOCUMENTS

| | | | |
|---|---|---|---|
| 7,744,740 | B2 | 6/2010 | Diehl |
| 2002/0012156 | A1 | 1/2002 | Varaprasad et al. |
| 2003/0121310 | A1* | 7/2003 | Tomura ................ G01N 27/419 73/31.05 |
| 2003/0121311 | A1* | 7/2003 | Tomura ................ G01N 27/419 73/35.05 |
| 2009/0038941 | A1* | 2/2009 | Stahl ................... G01N 27/4065 204/424 |
| 2011/0083490 | A1* | 4/2011 | Murakami ......... G01N 27/4071 73/31.05 |
| 2012/0167656 | A1* | 7/2012 | Verdier .............. G01N 27/4175 73/1.06 |

FOREIGN PATENT DOCUMENTS

| | | |
|---|---|---|
| DE | 102011005648 | 9/2012 |
| EP | 0 427 958 | 5/1991 |
| EP | 1365234 | 11/2003 |
| WO | WO 2006/084836 | 8/2006 |

\* cited by examiner

METHOD FOR ADJUSTING A GAS SENSOR

BACKGROUND OF THE INVENTION

1. Field of the Invention

The present invention relates to a method for adjusting a gas sensor.

2. Description of the Related Art

Adjusting a gas sensor is understood to mean in particular obtaining information concerning which measured value or which current the sensor actually delivers for a predefined measuring gas, or how this measured value or current correlates with an actual concentration of the gas component to be detected in a measuring gas.

A method for adjusting an amperometric gas sensor is already known from published German patent application document DE 10 2008 007 238 A1, the gas sensor having a diffusion barrier, a hollow chamber downstream from the diffusion barrier, and a pump cell. This method provides that the gas component to be determined, for example from a measuring gas, is pumped into the hollow chamber with the aid of the pump cell, the gas component to be determined is subsequently pumped out of the hollow chamber with the aid of the pump cell, and an adjustment value for the gas sensor is deduced from the resulting pump current and/or the variation of the pump current over time.

One disadvantage of this method is that adjustment values obtainable with the method are a function not only of the measured value or current which is measurable for a predefined measuring gas using this sensor, but also of further influencing variables, for example the volume of the measuring chamber and the volume of the diffusion barrier, of which the measured value or current which is measurable for a predefined measuring gas is not a direct function. As a result, only an erroneous adjustment of the amperometric gas sensor is possible using the method known from the related art.

BRIEF SUMMARY OF THE INVENTION

The object of the present invention, therefore, is to provide a method which allows an adjustment of the in particular amperometric gas sensor which is less error-prone or not at all error-prone.

According to the present invention, an adjustment of an in particular amperometric gas sensor is provided, i.e., a gas sensor which, with appropriate wiring, is suitable for delivering a measurable variable, in particular a current, for determining the concentration of a gas component in a measuring gas chamber.

According to the present invention, sensors of this type have an electrochemical pump cell, i.e., two electrodes which are connected to one another in an ion-conductive manner via an electrolyte, in particular a solid electrolyte, and between which a pump voltage may be applied. According to the present invention, such sensors also have a hollow chamber which is connected to a measuring gas chamber via a diffusion barrier.

According to the present invention, the measuring gas chamber is understood to mean the space, present outside the gas sensor, in which the gas to be tested is situated. According to the present invention, a diffusion barrier in the broadest sense is understood to mean a device which is able to limit a transport of gas, for example a diffusion and/or a flow, from the measuring gas chamber into the hollow chamber, for example a narrow open channel or a porous filling of a channel, or the like. The gas component may be oxygen, carbon monoxide, a hydrocarbon, a nitrogen oxide, or hydrogen, for example. The method is also suitable for other gas components and gas sensors.

According to the present invention, the electrochemical pump cell is provided for electrochemically pumping the gas component to be tested into or out of the hollow chamber. For this purpose, the hollow chamber has a design which in particular is adjacent to and/or enclosed by the solid electrolyte, and in particular a first electrode of the electrochemical pump cell is provided in the hollow chamber, or between the hollow chamber and the solid electrolyte. A second electrode of the electrochemical pump cell is in particular provided outside of and at a distance from the hollow chamber, in particular in the measuring gas or in a reference gas chamber which is completely or partially sealed off from the measuring gas.

According to the present invention, the method provides multiple pumping-in phases. A pumping-in phase is understood to mean in particular a continuous period of time in which an electrochemical transport into the hollow chamber of the type of gas to be tested takes place and/or is caused by an appropriate pump voltage that is applied and/or is present between the electrodes of the electrochemical pump cell. In multiple pumping-in phases, according to the present invention n or at least n pumping-in phases may be provided, where n may have the values 2, 3, 4, 5 for each of the two alternatives. In addition, any one of the larger integer values for n, for example 6, 7, etc., is possible for both alternatives, and is not explicitly noted here solely for the purpose of brevity.

According to the present invention, the method provides multiple pumping-out phases. A pumping-out phase is understood to mean in particular a continuous period of time in which an electrochemical transport of the type of gas to be tested from the hollow chamber takes place or is caused by an appropriate pump voltage that is applied and/or is present between the electrodes of the electrochemical pump cell. In multiple pumping-out phases, according to the present invention n or at least n pumping-out phases may be provided, where n may have the values 2, 3, 4, 5 for each of the two alternatives. In addition, any one of the larger integer values for n, for example 6, 7, etc., is possible for both alternatives, and is not explicitly noted here solely for the purpose of brevity. Providing multiple pumping-out phases results in the option, made use of according to the present invention, of obtaining a more extensive database for obtaining information for adjusting the gas sensor.

According to the present invention, it is provided that at least one feature, in particular a property, of the pump current, or a combination of multiple features, in particular a combination of multiple properties, which is/are detected during the pumping-out phases, is used to generate at least one piece of information for adjusting the gas sensor. The feature of the pump current that is detected during the pumping-out phases may in particular be a charge quantity that is pumped overall in the particular pumping-out phase, or a pump current, in particular a maximum or averaged pump current, during the pumping-out phase. These features have in common that they are used as a measure for the extent to which the hollow chamber is filled with the gas component to be detected at the beginning of the pumping-out phase.

The information for adjusting the gas sensor is understood in particular to mean information concerning which measured value or which current the sensor actually delivers for a predefined measuring gas, or how this measured value or current correlates with an actual concentration of the gas component to be detected in a measuring gas. In particular, the information may be the value of a limiting current of the electrochemical pumping out from the hollow chamber for a certain measuring gas composition, and/or the value of the diffusion resistance of the diffusion barrier for a certain measuring gas composition. Such an adjustment value may be provided in particular to correct the measured value delivered by the gas sensor in such a way that the measured value corresponds to the actual value of the variable to be measured. On the other hand, however, the information for adjusting the gas sensor may also be information concerning an aging state of the sensor and/or information concerning, and/or whether, the sensor in question is operating properly or whether a defect is present. The information may also concern the type of sensor in question.

The generation of the information may in particular be the ascertainment and/or computation of the information.

The present invention is based on the finding that the implementation of a method which allows an adjustment of the amperometric gas sensor which is less error-prone or not at all error-prone makes it possible for a parameter regarding the pumping-in to be predefined differently in different pumping-in phases. The available database is thus expanded in such a way that it is possible to extract a piece of information for adjusting the gas sensor which is largely or even solely a direct function only of the measured value or current which is measurable for a predefined measuring gas, using this sensor, and which is much less a function, or not a function at all, of further influencing variables, such as the volume of the measuring chamber and the volume of the diffusion barrier.

A critical factor is the variation of the parameter regarding the pumping-in in various pumping-in phases. As a result of this variation, it is ensured that in various pumping-in phases different fillings of the hollow chamber with the gas component to be tested are prepared, which allows the various pumping-out phases of different fillings of the hollow chamber with the gas component to be tested to be started, and thus allows new, nonredundant information to be obtained in each case in the various pumping-out phases, from which it is possible to extract a piece of information for adjusting the gas sensor which is largely or even solely a direct function only of the measured value or current which is measurable for a predefined measuring gas, using this gas sensor.

The parameter regarding the pumping-in may in particular be a pump current, for example a pump current which is constant during a pumping-in phase or which is averaged during a pumping-in phase, or, for example, a pump voltage, in particular a pump voltage which is constant during a pumping-in phase or which is averaged during a pumping-in phase, or a charge quantity that is pumped overall in a pumping-in phase, or the duration of a pumping-in phase. These parameters share the common feature that they quantitatively characterize the quantity of the gas component which is pumped into the hollow chamber in a pumping-in phase.

The method may thus be interpreted in such a way that different gas quantities are pumped into the hollow chamber, and an analysis is subsequently made concerning which portion of the pumped-in gas quantity may still be pumped out of the hollow chamber, and which portion has escaped in some other way. The desired information may be derived with higher precision from the totality of the data collected in this way. Against this background, it is preferred that a pumping-in phase chronologically precedes a pumping-out phase, and in particular each pumping-in phase precedes, in particular immediately precedes, a pumping-out phase in each case. Beginning with a pumping-in phase or beginning with a pumping-out phase, pumping-in phases and pumping-out phases may be carried out in alternation, for example, in particular in alternation in immediate succession.

For obtaining the information for adjusting the gas sensor, it is advantageous for a value of the parameter regarding a pumping-in phase $E_n$, which this parameter assumes during this pumping-in phase $E_n$, to be associated with each pumping-in phase $E_n$, and for a value of the feature of the pumping-out phase to be detected in subsequent pumping-out phase $A_n$.

In addition, it is advantageous to generate the information for adjusting the gas sensor on the basis of the data collected in this way, and on the basis of a functional relationship between the feature of the pump current during the pumping-out phases and the parameter regarding the pumping-in.

The functional relationship may be, for example, a polynomial, for example a first-, second-, or third-order polynomial or at least a first-, second-, or third-order polynomial. However, other functional relationships between the feature of the pump current during the pumping-out phases and the parameter regarding the pumping-in are also possible in principle, such as logarithmic functions.

Parameters of the functional relationship are advantageously obtained in this way, for example by analytical, for example unequivocal, computation of these parameters, or by evaluating underlying functional relationship f with the aid of a regression computation, in particular a fit, for example a regression computation according to the method of least squares.

In the case that a first-order polynomial is used as the functional relationship, two parameters are advantageously provided, and in the case of a second-order polynomial, three parameters are provided, and so forth.

The parameters obtained in this way are advantageously used to obtain the information for adjusting the gas sensor. This may be carried out on the basis of a computation with the aid of a computation rule r, for example with the aid of a first-, second-, third-, or higher-order polynomial. The computation rule may in particular be a polynomial whose variables are the parameters determined in advance. Other computation rules r are also possible in principle.

The voltage applied to the pump cell in particular is not constant for the duration of the method, and in particular the transition between pumping-in phases and pumping-out phases is associated with a change in the voltage applied to the pump cell. Since electrical charge carriers are displaceably present in and between the electrodes of the pump cell, a certain transport of electrical charge is already linked to the change in the voltage applied to the pump cell, even if electrochemical reactions at the electrodes of the pump cell do not result or have not yet resulted. Although the characteristics of this transient operation are often included in the ascertained feature of the pump current during the pumping-out phases, there is frequently little or no correlation with the sought information for adjusting the gas sensor. For this reason it is advantageous to determine electrical capacitance C of the pump cell in advance during manufacture of the gas sensor and/or within the scope of the method according to the present invention, and/or to take electrical capacitance C into account during the ascertainment of the information, in particular to compute same with the aid of computation rule r.

The information obtained for adjusting the gas sensor with the aid of the method according to the present invention is largely independent of the concentration of the gas component in the measuring gas. Nevertheless, the method may be even further optimized by carrying out the method while there is little or no fluctuation of this concentration of the gas component in the measuring gas. When the method is carried out in a gas sensor that is situated in the exhaust tract of an internal combustion engine or of a burner, this may be during a shutdown, for example. In addition, a phase in which the internal combustion engine is not supplied with fuel (coasting mode) is preferred for the same reasons.

The specific manner in which function f and/or computation rule r is/are selected depends on a number of influencing variables such as the type of sensor, the operating conditions, and the gas component. Studies by the present applicant have shown that a particularly good adjustment for a number of gas sensors is possible, using a certain function f and/or a certain computation rule r, when these gas sensors all have the same design, in particular when they have features, for example the limiting current of their pump cell, which are within a variance range of 5%, 10%, or 20%, for example. Thus, a certain function f and/or a certain computation rule r is/are associated with a certain type of sensor, and for example is/are permanently stored in a control unit for carrying out the method according to the present invention.

Moreover, the present invention relates to a control unit which is set up to carry out the method according to the present invention, and a sensor device composed of such a control unit and a gas sensor of the above-described type.

DETAILED DESCRIPTION OF THE INVENTION

Figure 1:
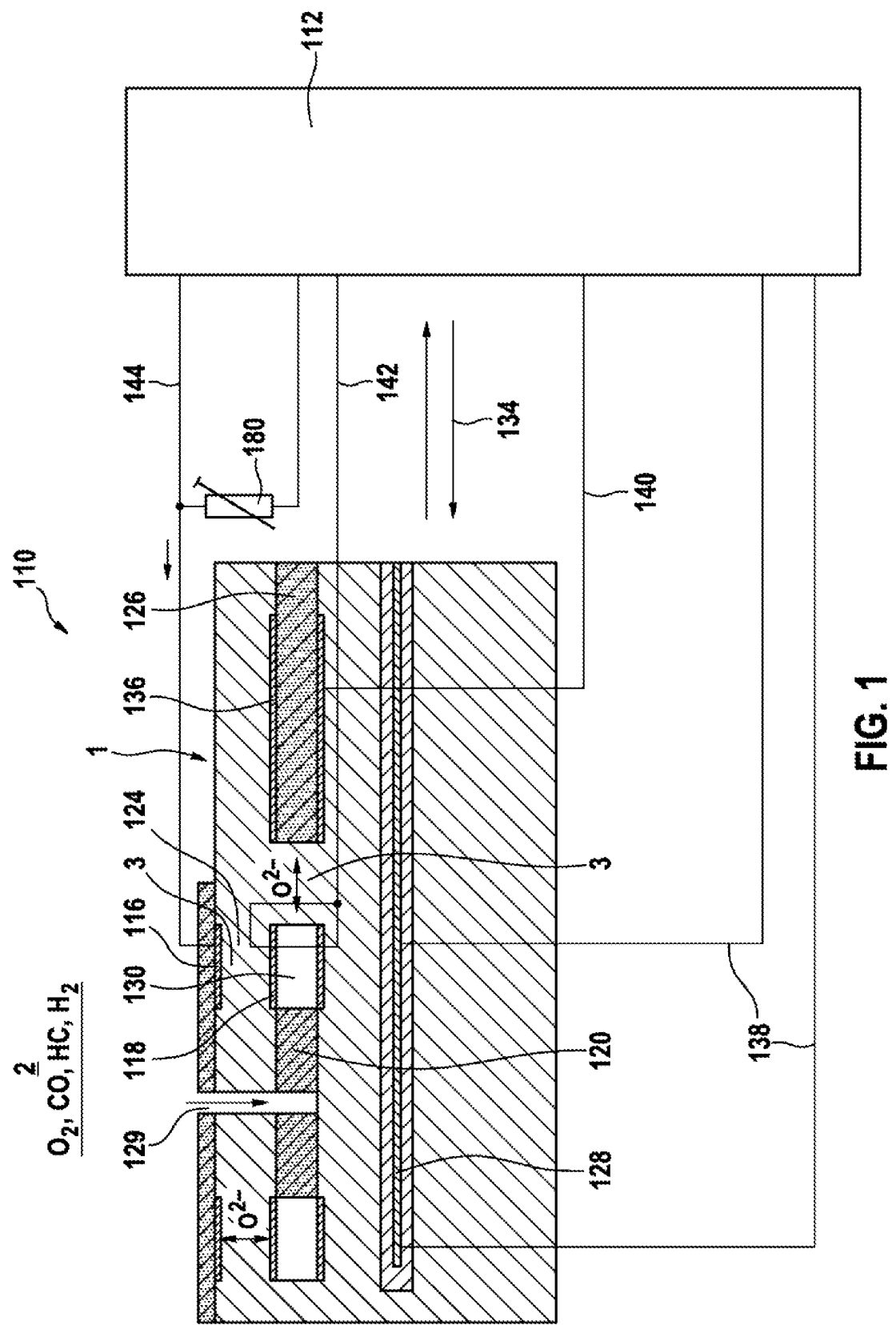
FIG. 1 shows one exemplary embodiment of a sensor device according to the present invention.

FIG. 1 illustrates one exemplary embodiment of a sensor device 110 according to the present invention. Sensor device 110 includes at least one gas sensor 1 for detecting at least a portion of at least one gas component of a gas in a measuring gas chamber 2, in particular for detecting oxygen in an exhaust gas of an internal combustion engine. Sensor element 1 includes a first electrode 116 and a second electrode 118. Second electrode 118 is connected to at least one hollow chamber 130, and is connected to measuring gas chamber 2 via at least one diffusion barrier 120. First electrode 116 and second electrode 118 are connected via at least one solid electrolyte 124. A voltage Up may be applied between first electrode 116 and second electrode 118, so that first electrode 116 and second electrode 118 together with solid electrolyte 124 form an electrochemical pump cell 3. Electrical current Ip flowing through pump cell 3 is detectable with time resolution.

First electrode 116 may be configured in particular as an external pump electrode, in particular in a two-cell gas sensor 1. First electrode 116 may be configured in particular as a reference electrode 136 in a one-cell gas sensor 1, not graphically illustrated here. As the external pump electrode, first electrode 116 may be situated in particular in a measuring gas chamber 2. First electrode 116, in particular as reference electrode 136, may be situated in particular in a further gas chamber, for example a reference gas chamber 126, i.e., in a gas chamber which is separated from measuring gas chamber 2 in a gas-tight or at least an essentially gas-tight manner. Second electrode 118 may be situated in hollow chamber 130, but may also be connected to hollow chamber 130 fluidically and/or via a gas connection. In addition, gas sensor 1 may include a heating element 128. Furthermore, gas sensor 1 may include an adjustment resistor 180. Adjustment resistor 180 may be used, for example with a measuring shunt, as a current divider for adjusting gas sensor 1, in particular for calibration. Sensor device 110 also has at least [one] control unit 112. Control unit 112 is set up to carry out a method according to the present invention for adjusting an amperometric gas sensor. Control unit 112 may be connected to gas sensor 1 via an interface 134, for example. However, control unit 112 may also be completely or partially integrated into gas sensor 1. However, control unit 112 may, for example, also be completely or partially integrated into other components, for example into a plug and/or an engine control system. Control unit 112 may, for example, include at least one impingement device in order to act on the electrodes, in particular first electrode 116 and/or second electrode 118 and/or a further electrode and/or a third electrode, for example a reference electrode 136, with current and/or voltage. The impingement device may be a voltage source and/or a current source, for example. In particular, a constant current source may be provided as the impingement device. The impingement device may in particular include electrical lines. For example, the impingement device may include in particular at least two heat supply lines 138, in particular for supplying heating element 128 with electrical voltage and/or electrical current, and/or a reference electrode supply line 140 and/or an inner electrode supply line 142 and/or an external pump electrode supply line 144. In addition, control unit 112 may optionally include at least one measuring device, for example at least one voltmeter and/or at least one ammeter. The measuring device is optionally set up in each case to measure a voltage or a current, for example to measure with time resolution a voltage that is present between first and second electrodes 116, 118, or, for example, to measure with time resolution a current flowing between first and second electrodes 116, 118, i.e., through pump cell 3. In particular, the measuring device may also be set up for further processing of the variable which is measured with time resolution, for example for integrating or averaging over a time interval, or for recognizing a maximum value of the variable in question in a time interval. However, control unit 112 may also optionally include at least one separate evaluation device, for example at least one separate data processing device, in which the measured variables are further processed as described. Furthermore, control unit 112 may optionally include at least one signal generator. Moreover, control unit 112 may optionally include at least one controller, for example at least one lock-in controller.

FIG. 1 illustrates in particular a two-cell gas sensor 1, in particular a broadband lambda sensor. In principle, the method according to the present invention may also be carried out using other gas sensors 1 as known from the related art. For example, one-cell gas sensors 1 may also be used. In a two-cell gas sensor 1, as may be used in particular in carrying out the method according to the present invention, first electrode 116 may be configured, for example, as reference electrode 136. Second electrode 118 may be configured, for example, as the inner pump electrode, in particular as the internal pump electrode. First electrode 116, in particular reference electrode 136, may in particular be connected to reference gas chamber 126. Second electrode 118, in particular the internal pump electrode, may in particular be connected to hollow chamber 130 and acted on with gas from measuring gas chamber 2 via a diffusion barrier 120. First electrode 116 and second electrode 118 may be connected in an ion-conductive manner via a solid electrolyte 124, for example.

FIG. 1 shows an example of a schematic design of a broadband lambda sensor. Gas sensor 1 may in particular include a gas inlet orifice 129. For example, a diffusion path of the gas, in particular of the gas component of the gas, for example oxygen, may lead from gas inlet orifice 129 through diffusion barrier 120, in particular through porous diffusion barrier 120, to second electrode 118, in particular the internal pump electrode, into hollow chamber 130. Solid electrolyte 124 may be made, in particular completely or predominantly, of partially or fully stabilized zirconium oxide, and electrodes 116, 118, 136 may be made, in particular completely or predominantly, of a cermet, for example a cermet containing platinum and partially or fully stabilized zirconium oxide.

Figure 2:
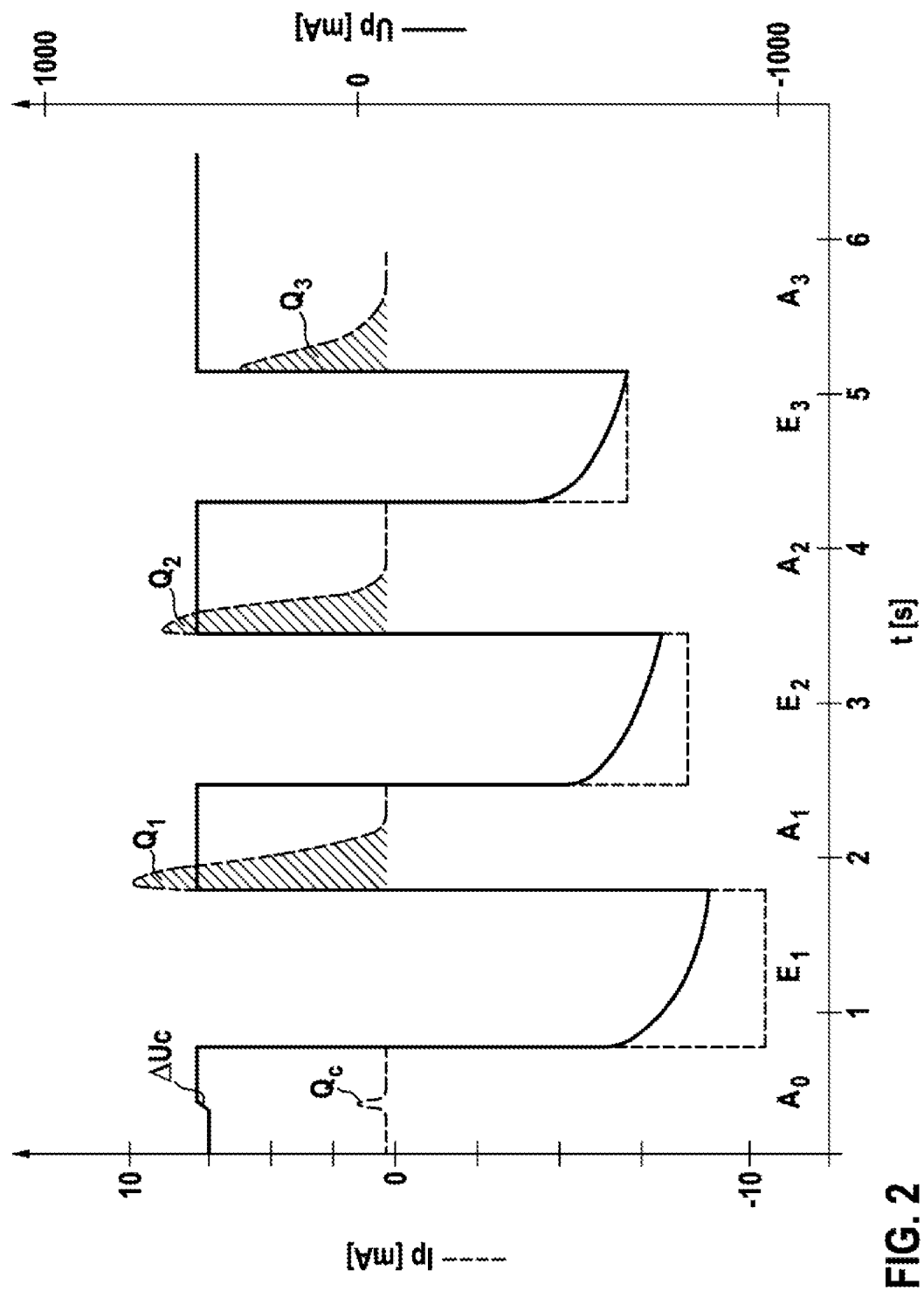
FIG. 2 shows the variation over time of the voltage applied to the pump cell and of the current flowing through the pump cell.

FIG. 2 shows one exemplary embodiment of the method according to the present invention which is carried out, for example, using gas sensor 1 shown in FIG. 1 or a gas sensor 1 described above. FIG. 2 shows voltage Up which is present at pump cell 3, i.e., between first electrode 116 and second electrode 118, and current Ip flowing through pump cell 3, i.e., between first electrode 116 and second electrode 118.

In a first phase $A_0$ of the method, a voltage Up is present at pump cell 3 whose magnitude and algebraic sign are suitable for continually electrochemically pumping out all molecules of the gas component which passes into hollow chamber 130 from measuring gas chamber 2 through diffusion barrier 120, for example, $Up_0 = 400$ mV or 700 mV or 400 mV to 700 mV. Electrical current Ip through pump cell 3, which in this phase is steady-state, represents limiting current $Ip_0$ of the electrochemical pumping out from hollow chamber 130 for the gas component concentration prevailing in measuring gas chamber 2.

Optionally, it may be provided that capacitance C of electrochemical pump cell 3 is determined in this phase of the method according to the present invention, or also in some other phase of the method according to the present invention. For this purpose, in particular electrical voltage Up which is present at pump cell 3 is changed, for example increased or decreased, by amount $\Delta Uc$, for example by a small amount such as 5 mV or 100 mV, or 5 mV at the most, or 100 mV at the most, or by 5 mV to 100 mV. Since the pumping out of the gas component from hollow chamber 130 takes place in the limiting current, varying pump voltage Up has no effect on the quantity of gas electrochemically transported in a steady-state manner out of or into hollow chamber 130. However, varying pump voltage [by] $\Delta Uc$ results in a charge transfer Qc within the electrochemical pump cell which from the standpoint of the measuring device is manifested as a temporarily increased/decreased pump current Ip, the integral of this temporary current increase corresponding to charge transfer Qc. It is provided that electrical capacitance C of the electrochemical pump cell is determined, in particular according to the equation $C = Qc/\Delta Uc.$ The phase of the method following first phase $A_0$ of the method in this example is a first pumping-in phase $E_1$. In this phase, a voltage Up is applied to electrochemical pump cell 3 for a defined period, for example for 100 ms to 1000 ms, in particular for 500 ms, in such a way that a constant pump current $Ip_1$ of approximately −10 mA, for example, results during this phase. In the process, in particular the concentration, i.e., the partial pressure, of the gas component in hollow chamber 130 increases.

The phase of the method following first pumping-in phase $E_1$ in this example is a first pumping-out phase $A_1$. In this phase, for a defined period, for example for 100 ms to 1000 ms, in particular for 500 ms, once again value $Up_0 = 500$ mV or 700 mV for voltage Up is predefined which causes electrochemical transport of the gas component from hollow chamber 130. Pump current Ip flowing during this phase is initially relatively high, since an increased quantity of the gas component is initially present in hollow chamber 130. As a result of pumping out this gas component, Ip decreases, for example to limiting current $Ip_0$, measured at the outset, of the electrochemical pumping out from hollow chamber 130 at the gas component concentration prevailing in measuring gas chamber 2. In this example, the value of pump current Ip flowing during this pumping-out phase $A_1$ is computationally integrated into the value of charge quantity $Q_1$ by the measuring device or by the separate evaluation device. This charge quantity $Q_1$ is preferably corrected for distortions which occur, for example, during the pumping-out phase due to gas transport through diffusion barrier 120. For this purpose, in particular the product of limiting current $Ip_0$ and the time which elapses until pump current Ip has dropped to a certain value, for example $1.05 * Ip_0$, is used.

In this example, a second pumping-in phase $E_2$, a second pumping-out phase $A_2$, a third pumping-in phase $E_3$, and a third pumping-out phase $A_3$ follow in succession in a manner similar to first pumping-in phase $E_1$ and first pumping-out phase $A_1$, except that pumping-in currents $Ip_2$ and $Ip_3$ differ from $Ip_1$ and differ from one another, for example [with a value of] approximately 7.5 mA and approximately 5 mA, respectively. Of course, other pumping-in currents Ip are also possible. Similarly, in pumping-out phases $A_2$ and $A_3$, charge quantities $Q_2$ and $Q_3$, respectively, are ascertained which differ from $Q_1$, for example which are smaller than $Q_1$.

Further pumping-in and pumping-out phases may be similarly provided, for example a fourth pumping-in phase $E_4$ in which once again a pumping-in current $Ip_4$ is predefined which differs from pumping-in currents $Ip_1$, $Ip_2$, $Ip_3$, and a further, subsequent pumping-out phase in which charge quantity $Q_4$ is determined. Further phases are possible, and are not individually described in detail here solely for the purpose of brevity.

It is provided in this example that the described phases have the same duration, although it is also possible for pumping-in phases and pumping-out phases to have differing durations. It is provided in this example that the described phases follow one another in direct succession. However, it is also possible to wait for a period of time, for example several milliseconds, between the individual phases.

In this example, predefined parameter $P_{in}$, provided according to the present invention, regarding the pumping-in is a constant pumping-in current Ip. However, other variables may also be used for parameter $P_{in}$ regarding the pumping-in, for example a pump voltage Up present during pumping-in phase E or a pumping duration t. In other respects, the method may be carried out according to the example, in which case in contrast to the example, this variable is varied from pumping-in phase to pumping-in phase.

The feature, provided according to the present invention, of the pump current during pumping-out phases $M_{out}$, on the basis of which at least one piece of information I for adjusting gas sensor 1 is generated, in the present example is charge quantity Q which flows through pump cell 3 during the pumping-out phase. However, other variables of this feature $M_{out}$ may be used, for example maximum pump current Ip occurring in a pumping-out phase, or pump current Ip occurring after a certain time period, or the time which elapses until pump current Ip has dropped to a predefined value, or the time which elapses until the gas concentration in hollow chamber 130 has dropped to a predefined value. The latter may also be ascertained, for example, with the aid of an additional, for example potentiometrically operated, electrochemical cell which in each case includes a second electrode 118 in hollow chamber 130 and a first electrode 116 in measuring gas chamber 2, or a first electrode 136 in reference gas chamber 126.

Figure 3:
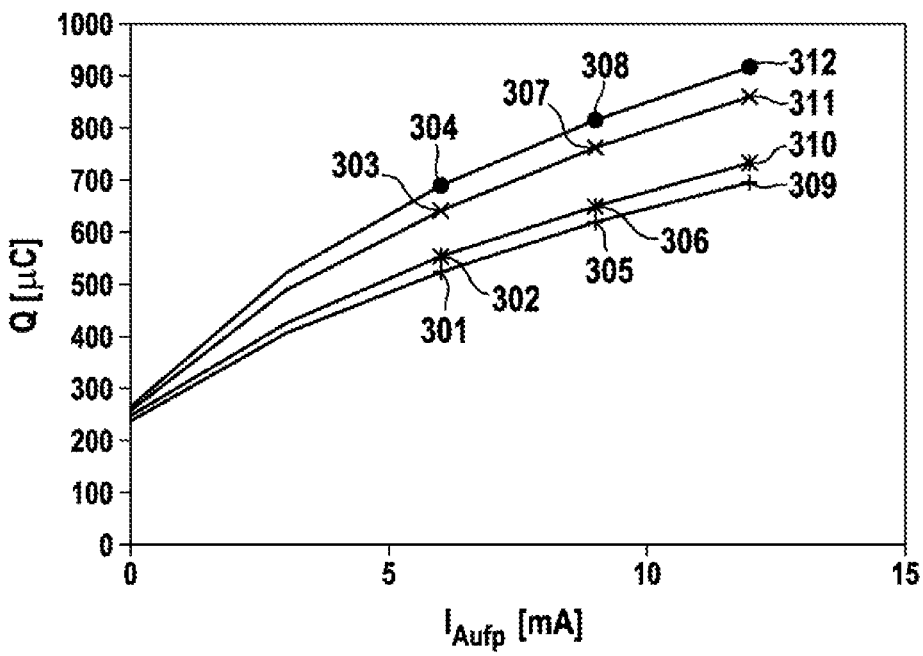
FIG. 3 shows the dependency of charge quantity Q pumped during a pumping-out phase on a current during preceding pumping-in phase Ip for various gas sensors.

According to the present invention, using the method, in each case a value of the feature of the pump current during pumping-out phases $M_{out, 1}$, $M_{out, 2}$, $M_{out, 3}$, ... is ascertained for predefined values of parameter $P_{in, 1}$, $P_{in, 2}$, $P_{in, 3}$ ... regarding the pumping-in. In this example, parameter $P_{in}$ regarding the pumping-in is pump current Ip, which is held constant, and in this example the feature of the pump current during pumping-out phases $M_{out}$ is charge quantity Q. Various examples of value pairs 300, 301, 302, ... 312 ascertained by gas sensors of one design type to be adjusted are illustrated in FIG. 3.

In another method step in this example, for generating information I for adjusting gas sensor 1, a functional relationship f is assumed which maps parameter $P_{in}$ regarding the pumping-in onto the feature of the pump current during pumping-out phases $M_{out}$. In the present example this is a polynomial, in particular for the function $$M_{out} = a\, P_{in}^2 + b\, P_{in} + c.$$

Since in this example three value pairs for $P_{in}$ and $M_{out}$ have been ascertained for each gas sensor, unique solutions for parameters a, b, and c may be ascertained, for example by solving the resulting linear system of equations. In cases for which this procedure is not possible, for example because for a gas sensor more value pairs for $P_{in}$ and $M_{out}$ have been ascertained than there are parameters a, b, c present, regression computations, in particular fits, for example a regression computation according to the method of least squares, may be carried out to determine parameters a, b, c.

Other functional relationships f may also be similarly used as the basis, for example first- or higher-order polynomials or functions which reflect a saturation behavior, for example the function $M_{out} = \log(f'(P_{in}))$ or the like, where log is an in particular natural logarithm, and f' is a functional relationship of the type described above with regard to f.

In another method step of this example, for generating information I for adjusting the gas sensor, a computation rule r is assumed, with the aid of which information I for adjusting the gas sensor is computed based on previously obtained parameters a, b, c, but in the present example based solely on the two parameters a and c and not b. In this example, the value of previously determined capacitance C of electrochemical pump cell 3 is also included in this function. In the present example, this computation rule r is the following function:

$$I = 0.37a^2 + 1.8a - 3.1c + 9.0C.$$

In principle, other types of computation rules r may be used as the basis. The coefficients of the appropriate computation rule may be ascertained, for example, in simple test series. In particular, the coefficients of the appropriate computation rule may be found in test series which are to be carried out only once for a type of sensor, and in which the coefficients are optimized in such a way that the resulting information of a variable to be measured within the scope of the test series, for example the limiting current of the gas sensor during operation in ambient air, has the best possible correspondence. In optimizing the coefficients, analytical computations or regression computations, for example, may be resorted to, so that the coefficients are optimized reliably, with a reasonable level of effort, and without difficulties.

It is provided to store the value of I ascertained in this way, for example, in control unit 112 associated with sensor unit 110, and to use this value in evaluating pump currents Ip measured by the measuring device during operation of gas sensor 1, in particular to compute measured pump currents Ip using value I, in particular to divide by value I.

Figure 4:
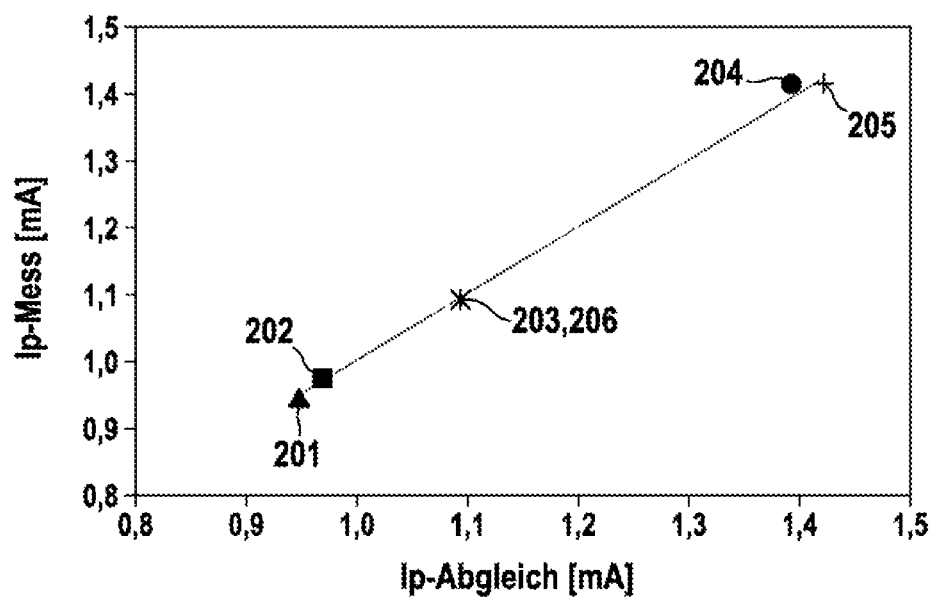
FIG. 4 shows measured limiting currents as a function of information ascertained using the method according to the present invention, for various gas sensors.

The method according to the present invention has been carried out for six examples of gas sensors 1 having diffusion barriers 120 of differing seal-tightness, so that a value I has been ascertained for each gas sensor 1. The method has been carried out using a measuring gas 2 which was selected differently for each gas sensor 1, but otherwise in an arbitrary manner. In addition, for purposes of comparison, limiting current $Ip_0$ has been ascertained during operation in ambient air for each gas sensor. Resulting value pairs 201, 202, ... 206 are plotted in FIG. 4. This plot shows a high correlation of information I, ascertained in an unknown measuring gas with the aid of the method according to the present invention, with the limiting current measured in a known measuring gas.

What is claimed is:

1. A method for adjusting a gas sensor configured to determine a concentration of a gas component in a measuring gas chamber, the gas sensor having at least one hollow chamber which is connected to the measuring gas chamber via a diffusion barrier, and the gas sensor having at least one electrochemical pump cell for electrochemically pumping the gas component into and out of the hollow chamber, the method comprising:
    providing at least two pumping-in phases in which the gas component is pumped into the hollow chamber by the electrochemical pump cell, wherein a characteristic parameter regarding the pumping-in is predefined differently in the at least two pumping-in phases;
    providing at least two pumping-out phases in which the gas component is pumped out of the hollow chamber by the electrochemical pump cell; and
    generating, on the basis of at least one feature of the pump current during the at least two pumping-out phases, an adjustment value of (i) a limiting current of the electrochemical pumping-out from the hollow chamber for a defined measuring gas composition or (ii) a diffusion resistance of the diffusion barrier for a defined measuring gas composition.

2. The method as recited in claim 1, wherein:
    at least three pumping-in phases are provided, in which the gas component is pumped into the hollow chamber by the electrochemical pump cell;
    at least three pumping-out phases are provided, in which the gas component is pumped out of the hollow chamber by the electrochemical pump cell; and
    the characteristic parameter regarding the pumping-in is predefined differently in the at least three pumping-in phases.

3. The method as recited in claim 1, wherein the characteristic parameter regarding the pumping-in is: (i) a pump current which is constant during a pumping-in phase; (ii) a pump current which is averaged during the pumping-in phase; (iii) a pump voltage which is constant during the pumping-in phase; (iv) a pump voltage which is averaged during the pumping-in phase; (v) a charge quantity which is pumped in the pumping-in phase; or (vi) a duration of the pumping-in phase.

4. The method as recited in claim 1, wherein the at least one feature of the pump current during the pumping-out is (i) a charge quantity which is pumped in a pumping-out phase, (ii) a maximum pump current during the pumping-out phase, (iii) an averaged pump current during the pumping-out phase, or (iv) a duration of the pumping-out phase.

5. The method as recited in claim 4, wherein each pumping-in phase is characterized by a value of the corresponding characteristic parameter, and wherein each pumping-in phase chronologically immediately precedes a corresponding pumping-out phase which is characterized by a value of the at least one feature of the pump current during the pumping-out phase, and wherein the adjustment value for adjusting the gas sensor is generated on the basis of a functional relationship between the at least one feature of the pump current during the pumping-out phases and the characteristic parameter regarding the pumping-in.

6. The method as recited in claim 5, wherein the functional relationship between values of the at least one feature of the pump current during the pumping-out phases and values of the characteristic parameter regarding the pumping-in is at least a second-order polynomial.

7. The method as recited in claim 6, wherein the values of the at least one feature of the pump current during the pumping-out phases and the values of the characteristic parameter regarding the pumping-in are taken into account by (i) an unequivocal evaluation of the functional relationship or (ii) an evaluation of the functional relationship with the aid of a regression computation, wherein at least three parameters of the functional relationship are determined.

8. The method as recited in claim 7, wherein for ascertaining the adjustment value for adjusting the gas sensor, the at least three parameters of the functional relationship are computed with the aid of a computation rule which is a polynomial whose variables are the at least three parameters, and wherein the polynomial has coefficients which are empirically ascertained for the type of the gas sensor.

9. The method as recited in claim 6, wherein the value of an electrical capacitance of the electrochemical pump cell is computed during the ascertainment of the adjustment value for adjusting the gas sensor.

10. The method as recited in claim 5, wherein the value of an electrical capacitance of the electrochemical pump cell is computed during the ascertainment of the adjustment value for adjusting the gas sensor.

11. The method as recited in claim 5, wherein the gas sensor is situated in an exhaust tract of an internal combustion engine or a burner.

12. The method as recited in claim 11, wherein the method is carried out during a shutdown of the engine or a shutdown of the burner.

13. The method as recited in claim 12, wherein the method is carried out multiple times at essentially regular intervals.

14. A computer-readable data storage medium storing a computer program having program codes which, when executed on a computer, performs a method for adjusting a gas sensor for determining a concentration of a gas component in a measuring gas chamber, the gas sensor having at least one hollow chamber which is connected to the measuring gas chamber via a diffusion barrier, and the gas sensor having at least one electrochemical pump cell for electrochemically pumping the gas component into and out of the hollow chamber, the method comprising:
   providing at least two pumping-in phases in which the gas component is pumped into the hollow chamber by the electrochemical pump cell, wherein a characteristic parameter regarding the pumping-in is predefined differently in the at least two pumping-in phases;
   providing at least two pumping-out phases in which the gas component is pumped out of the hollow chamber by the electrochemical pump cell; and
   generating, on the basis of at least one feature of the pump current during the at least two pumping-out phases, an adjustment value of (i) a limiting current of the electrochemical pumping-out from the hollow chamber for a defined measuring gas composition or (ii) a diffusion resistance of the diffusion barrier for a defined measuring gas composition.

15. A control unit for adjusting a gas sensor configured to determine a concentration of a gas component in a measuring gas chamber, the gas sensor having at least one hollow chamber which is connected to the measuring gas chamber via a diffusion barrier, and the gas sensor having at least one electrochemical pump cell for electrochemically pumping the gas component into and out of the hollow chamber, the control unit comprising:
   circuitry that is programmed with a program that, when executed by the circuitry, causes the circuitry to perform the following:
      control at least two pumping-in phases in which the gas component is pumped into the hollow chamber by the electrochemical pump cell, wherein a characteristic parameter regarding the pumping-in is predefined differently in the at least two pumping-in phases;
      control at least two pumping-out phases in which the gas component is pumped out of the hollow chamber by the electrochemical pump cell;
      generate, on the basis of at least one feature of the pump current during the at least two pumping-out phases, an adjustment value of (i) a limiting current of the electrochemical pumping-out from the hollow chamber for a defined measuring gas composition or (ii) a diffusion resistance of the diffusion barrier for a defined measuring gas composition; and
      store the adjustment value for adjusting the gas sensor.

* * * * *